United States Patent [19]

Jones et al.

[11] Patent Number: 4,519,717
[45] Date of Patent: May 28, 1985

[54] ON-STREAM CLOUD POINT ANALYZER

[75] Inventors: Hugh D. Jones, Chicago; Steven J. Martinich, Wheaton, both of Ill.

[73] Assignee: GCA Corporation, Bedford, Mass.

[21] Appl. No.: 385,936

[22] Filed: Jun. 7, 1982

[51] Int. Cl.³ .................. G01N 21/17; G01N 25/12
[52] U.S. Cl. ................................. 374/17; 356/434; 374/20
[58] Field of Search ............... 374/27, 17, 19, 20; 356/434, 440; 364/579, 580, 500; 73/27

[56] References Cited

U.S. PATENT DOCUMENTS

| | | | |
|---|---|---|---|
| 3,031,880 | 5/1962 | Findlay | 374/17 |
| 3,143,876 | 8/1964 | Wallgren | 374/17 |
| 3,174,824 | 3/1965 | Lupfer | 250/573 X |
| 3,187,557 | 6/1965 | Holbourne | 356/441 X |
| 3,457,772 | 7/1969 | Chassagne et al. | 374/17 |
| 3,545,254 | 12/1970 | Chassagne et al. | 374/17 |
| 4,216,669 | 8/1980 | Harding, Jr. | 374/20 |
| 4,240,284 | 12/1980 | Nguyen | 374/20 |

FOREIGN PATENT DOCUMENTS

| | | |
|---|---|---|
| 0041458 | 9/1981 | European Pat. Off. . |
| 0914320 | 1/1963 | United Kingdom . |
| 1197568 | 7/1970 | United Kingdom . |
| 1438754 | 6/1976 | United Kingdom . |

*Primary Examiner*—Daniel M. Yasich
*Attorney, Agent, or Firm*—Henry D. Pahl, Jr.

[57] ABSTRACT

Liquid hydrocarbon samples from a mainstream are diverted through a sample cell in cooling chamber. An optical cloud point detector signals a microprocessor-based control system which controls the charging and cooling of the cell. Cloud point reference level is continuously updated. After each measurement cycle, the control system readjusts the cooling power so that the time interval between the end of the flush cycle and cloud point detection is brought within a predetermined range. The control system switches between several distinct modes of operation automatically.

5 Claims, 26 Drawing Figures

FIG.4

| 4A | 4B | 4C |
|----|----|----|
| 4D | 4E | 4F |

FIG.5

| 5A | 5B |
|----|----|
| 5C | 5D |

FIG.6

| 6A | 6B |
|----|----|
| 6C | 6D |

*BYT 0 TO 440H                FIG. 7A
0000H=C3H 40H 00H 00H 00H 00H 00H 00H 00H 00H 00H 00H 00H 00H 00H 00H
0010H=00H 00H 00H 00H 00H 00H 00H 00H 00H 00H 00H 00H 00H 00H 00H 00H
0020H=00H 00H 00H 00H 00H 00H 00H 00H 00H 00H 00H 00H 00H 00H 00H 00H
0030H=00H 00H 00H 00H 00H 00H 00H 00H 00H 00H 00H 00H C3H B6H 00H 00H
0040H=31H FFH 30H AFH 32H 02H 38H 3EH FFH 32H 01H 38H CDH ACH 00H 3EH
0050H=04H 32H 01H 38H CDH ACH 00H CDH F7H 03H AFH 32H 01H 38H CDH ACH
0060H=00H 3EH 04H 32H 01H 38H CDH ACH 00H CDH 9DH 03H 31H FFH 30H F3H
0070H=AFH 32H 00H 30H 32H 04H 30H 32H 05H 30H 32H 0BH 30H 32H 0AH 30H
0080H=32H 11H 30H 32H 10H 30H 3EH 37H 47H 32H 01H 30H 32H 02H 38H 3EH
0090H=11H 32H 01H 38H CDH 6AH 01H 78H C6H 0AH FEH 91H C2H 88H 00H 32H
00A0H=01H 30H 32H 02H 38H 3EH 1BH 30H FBH C3H D5H 01H 06H 08H CDH 6AH
00B0H=01H 05H C2H AEH 00H C9H F5H C5H D5H E5H 2AH 0EH 30H 23H 22H 0EH
00C0H=30H 2AH 02H 30H 23H 22H 02H 30H 3EH 1BH 30H E1H D1H C1H F1H FBH
00D0H=C9H 3AH 10H 30H 1FH D2H E4H 00H 3AH 11H 30H 3CH FEH 79H CAH E4H
00E0H=00H 32H 11H 30H 21H 00H 00H 22H 02H 30H 2AH 02H 30H 7BH BDH C2H
00F0H=EAH 00H 7AH BCH C2H EAH 00H AFH 32H 01H 38H 06H 10H CDH 6AH 01H
0100H=05H C2H FDH 00H CDH B7H 02H 7CH FEH 07H DAH 24H 01H 3EH 13H 32H
0110H=01H 38H AFH 7CH 1FH 67H 7DH 1FH 6FH EBH CDH B7H 02H 7DH 93H 7CH
0120H=9AH DAH 1AH 01H 22H 06H 30H 22H 08H 30H AFH 32H 01H 38H 32H 0BH
0130H=30H 21H 00H 00H 22H 02H 30H C9H AFH 32H 00H 30H 3EH 01H 32H 01H
0140H=38H CDH 6AH 01H 3EH 10H 32H 01H 38H 2AH 02H 30H 3EH 5FH 95H 3EH
0150H=00H 9CH DAH 75H 01H 3EH 55H 95H 3EH 00H 9CH D2H A3H 01H AFH 32H
0160H=04H 30H 3EH 01H 32H 0AH 30H C3H D5H 01H 21H 00H 00H 11H 01H 00H
0170H=19H D2H 70H 01H C9H 3AH 0AH 30H 1FH DAH 9BH 01H AFH 3AH 01H 30H
0180H=C6H 0CH FEH 91H DAH 89H 01H 3EH 91H 32H 01H 30H 32H 02H 38H AFH
0190H=32H 04H 30H 3EH 01H 32H 0AH 30H C3H D5H 01H 3AH 01H 30H C6H 02H
01A0H=C3H 82H 01H 3AH 04H 30H D6H 01H 32H 04H 30H D2H D5H 01H 3AH 0AH
01B0H=30H 1FH DAH CDH 01H AFH 3AH 01H 30H D6H 14H D2H BFH 01H AFH 32H
01C0H=01H 30H 32H 02H 38H 3EH 01H 32H 04H 30H C3H D5H 01H 3AH 01H 30H
01D0H=D6H 03H C3H BBH 01H 11H 19H 00H CDH D1H 00H 3AH 10H 30H 1FH D2H
01E0H=03H 02H 3AH 11H 30H FEH 78H CAH C6H 02H 3AH 00H 38H 47H E6H 10H
01F0H=CAH FAH 01H AFH 32H 10H 30H C3H C6H 02H 78H E6H 04H C2H 12H 02H
0200H=C3H 6CH 00H 3AH 00H 38H 47H E6H 10H C2H C6H 02H 78H E6H 04H C2H
0210H=82H 03H CDH B7H 02H E5H EBH 2AH 06H 30H 7DH 93H 5FH 7CH 9AH E1H
0220H=D2H 29H 02H 22H 06H 30H C3H 2FH 02H 3EH 0FH BBH DAH 38H 01H 2AH
0230H=02H 30H 3AH 0BH 30H 1FH DAH 4FH 02H 7DH FEH 5FH C2H 4FH 02H 3EH
0240H=01H 32H 06H 30H 3AH 01H 30H C6H 02H 32H 01H 30H 32H 02H 38H 3AH
0250H=05H 30H 1FH DAH 5CH 02H 7DH FEH 55H CAH 96H 02H 3EH B4H BDH C2H
0260H=DBH 01H 3EH 00H BCH C2H DBH 01H 3EH 12H 32H 01H 38H 3AH 00H 30H
0270H=3CH 32H 00H 30H FEH 01H CAH 96H 02H FEH 02H CAH A3H 02H 3EH 48H
0280H=32H 01H 30H 32H 02H 38H AFH 32H 00H 30H 32H 0AH 30H 11H 1CH 02H
0290H=CDH D1H 00H C3H DBH 01H 3EH 01H 32H 05H 30H 3AH 01H 30H C6H 14H
02A0H=D2H A5H 02H 3EH 91H 32H 01H 30H 32H 02H 38H AFH 32H 04H 30H 3EH
02B0H=01H 32H 0AH 30H C3H D5H 01H 3AH 00H 38H 1FH DAH B7H 02H 2AH 01H
02C0H=3EH 7CH E6H 0FH 67H C9H F3H 3EH 19H 32H 01H 30H 32H 02H 38H 21H
02D0H=00H 00H 22H 02H 30H 22H 0EH 30H 3EH 1BH 30H FBH 3EH 11H 32H 01H
02E0H=38H 11H B4H 00H CDH D1H 00H AFH 32H 11H 30H 3AH 10H 30H 1FH D2H
02F0H=1BH 03H 3AH 00H 38H 47H E6H 10H CAH 02H 03H AFH 32H 10H 30H C3H
0300H=C6H 02H 7SH E6H 04H C2H 0BH 03H C3H 6CH 00H 2AH 0EH 30H 11H B0H
0310H=04H 7BH 95H 7AH 9CH DAH D5H 01H C3H 2AH 03H 3AH 00H 38H 47H E6H
0320H=10H CAH 2AH 03H 7SH E6H 04H C2H 82H 03H CDH B7H 02H E5H EBH 2AH
0330H=06H 30H 7DH 93H 5FH 7CH 9AH E1H D2H 41H 03H 22H 06H 30H C3H 47H
0340H=03H 3EH 0FH BBH DAH 64H 03H 2AH 02H 30H 7DH FEH 3CH C2H E7H 02H
0350H=3AH 01H 30H C6H 05H 32H 01H 30H 32H 02H 38H 21H 00H 00H 22H 02H
0360H=30H C3H E7H 02H 3EH 01H 32H 01H 38H CDH 6AH 01H 3EH 11H 32H 01H
0370H=38H 3AH 10H 30H 1FH DAH D5H 01H AFH 32H 01H 30H 32H 02H 38H C3H
0380H=E1H 02H F3H AFH 32H 11H 30H 3CH 32H 10H 30H 21H 00H 00H 22H 0EH

```
0390H=30H 3EH 1BH 30H FBH C3H C6H 02H 04H 00H FFH 55H AAH 3AH 98H 03H
03A0H=47H 11H F1H 30H 3AH 9CH 03H 4FH 21H 00H 30H 71H 23H 7DH 93H 7CH
03B0H=9AH DAH ABH 03H 21H 00H 30H 7EH B9H C2H F6H 03H 23H 7DH 93H 7CH
03C0H=9AH DAH 87H 03H 21H 98H 03H 05H CAH D6H 03H 7DH 80H 6FH 7CH CEH
03D0H=00H 67H 7EH C3H A7H 03H 21H 00H 30H 75H 23H 7DH 93H 7CH 9AH DAH
03E0H=D9H 03H 21H 00H 30H 0EH 00H 7EH B9H C2H F6H 03H 23H 0CH 7DH 93H
03F0H=7CH 9AH DAH E7H 03H C9H 76H 11H 39H 04H 21H 00H 00H D5H 01H 00H
0400H=00H 11H 00H 00H 7BH 86H 5FH 7AH CEH 00H 57H 79H CEH 00H 4FH EBH
0410H=E3H 2BH 7DH 84H DAH 1AH 04H CAH 20H 04H E3H EBH 23H C3H 04H 04H
0420H=E3H EBH E1H 21H 39H 04H 7BH BEH C2H 38H 04H 23H 7AH BEH C2H 38H
0430H=04H 23H 79H BEH C2H 38H 04H C9H 76H E7H 4FH 01H 00H 00H 00H 00H
0440H=00H
```

FIG. 7B

ON-STREAM CLOUD POINT ANALYZER

REFERENCE TO MICROFICHE APPENDIX

Incorporated herein by reference is a microfiche appendix consisting of one card containing 22 pages of software listings.

BACKGROUND OF THE INVENTION

The invention relates generally to analysis of the properties of liquid hydrocarbons, and more particularly to refinery process control and test apparatus for determining the temperature at which wax crystals first appear in a liquid hydrocarbon sample.

In the refining of certain liquid hydrocarbons such as diesel and fuel oil, wax molecules are found to be present in varying concentrations and forms at different stages of the refining process. Wax can be removed to a large extent by cooling the product to the point where the wax crystallizes and precipitates. The point at which wax crystals begin to form is referred to in the art as the cloud point, characterized by a rapid change in the optical characteristics of the liquid. In order to control the amount of wax remaining in a liquid hydrocarbon product to meet industry specifications for a given type of fuel oil for example, it is important to know the precise cloud point of the liquid hydrocarbon being produced. However, cloud points vary widely with the type of liquid hydrocarbon and are incapable of precise prediction without actually sampling the feedstock and testing its cloud point. Cloud point temperature is used in process control. The amount of wax remaining in the product may affect its quality and indirectly the price it can command in the marketplace. Inadvertently precipitating out far more wax than is required by the specifications for a given fuel oil, for example, can result in selling a very high quality fuel oil at the wrong price. Cooling large quantities of refinery product to remove wax is a costly undertaking requiring huge refrigeration units and tankage requirements. By increasing the accuracy and frequency of cloud point measurement, the refinery can control the product more closely with respect to sales specifications, thus optimizing quality control and maximizing the refinery's more profitable fractions.

In the past, cloud points have been analyzed in refineries by laboratory technicians. In many cases, samples are taken only once per shift. Meanwhile process control variables can range far from the optimum level. One of the major problems facing refinery companies is the measurement of cloud point of straight run products produced from a number of different crudes with differing characteristics. With frequently varying feedstock properties, the cloud point may change abruptly. Moreover, because of the varying optical properties of the feedstock, the threshold for optical detection of cloud point may also vary abruptly.

SUMMARY OF THE INVENTION

The general purpose of the invention is to sample a liquid hydrocarbon stream repeatedly to monitor cloud point temperatures with an updated detection threshold in a system with automatic control of the sample charge, dump and flush modes.

These and other objects are achieved in the microprocessor-controlled system according to the invention. Liquid hydrocarbon samples from a mainstream are diverted through a test cell in a Peltier cooling chamber. An optical cloud point detector signals a microprocessor-based control system which controls the charging and cooling of the cell. Cloud point threshold is continuously updated. In one mode, after each measurement cycle, the control system readjusts the cooling power so that the time interval between the end of the flush cycle and cloud point detection is brought within a predetermined range. The control system switches between several distinct modes of operation automatically. In another mode, the cooling rate is progressively increased to a point where in the absence of a cloud, the sample is automatically dumped. If a cloud is detected in this mode, the same cooling rate can be applied in the first mode. Onstream cloud point monitoring in applications ranging from hydro skimming to hydro conversion permits continuous updating of process control variables based on changes in cloud point resulting in more cost effective quality control of a wide range of products with varying specifications.

BRIEF DESCRIPTION OF THE DRAWING

FIG. 5, comprised of FIGS. 5A–5D, is a schematic circuit diagram of the central processing unit (CPU) printed circuit board (PCB) of FIG. 4.

FIGS. 7A and 7B is a read only memory table of machine code in hexadecimal digits.

Microfiche Appendix 1 consists of a complete assembler listing of all software instructions in the standard format for Intel 8085 microprocessors used in conjunction with the microprocessor control system according to the invention.

DESCRIPTION OF THE PREFERRED EMBODIMENT

Figure 1:
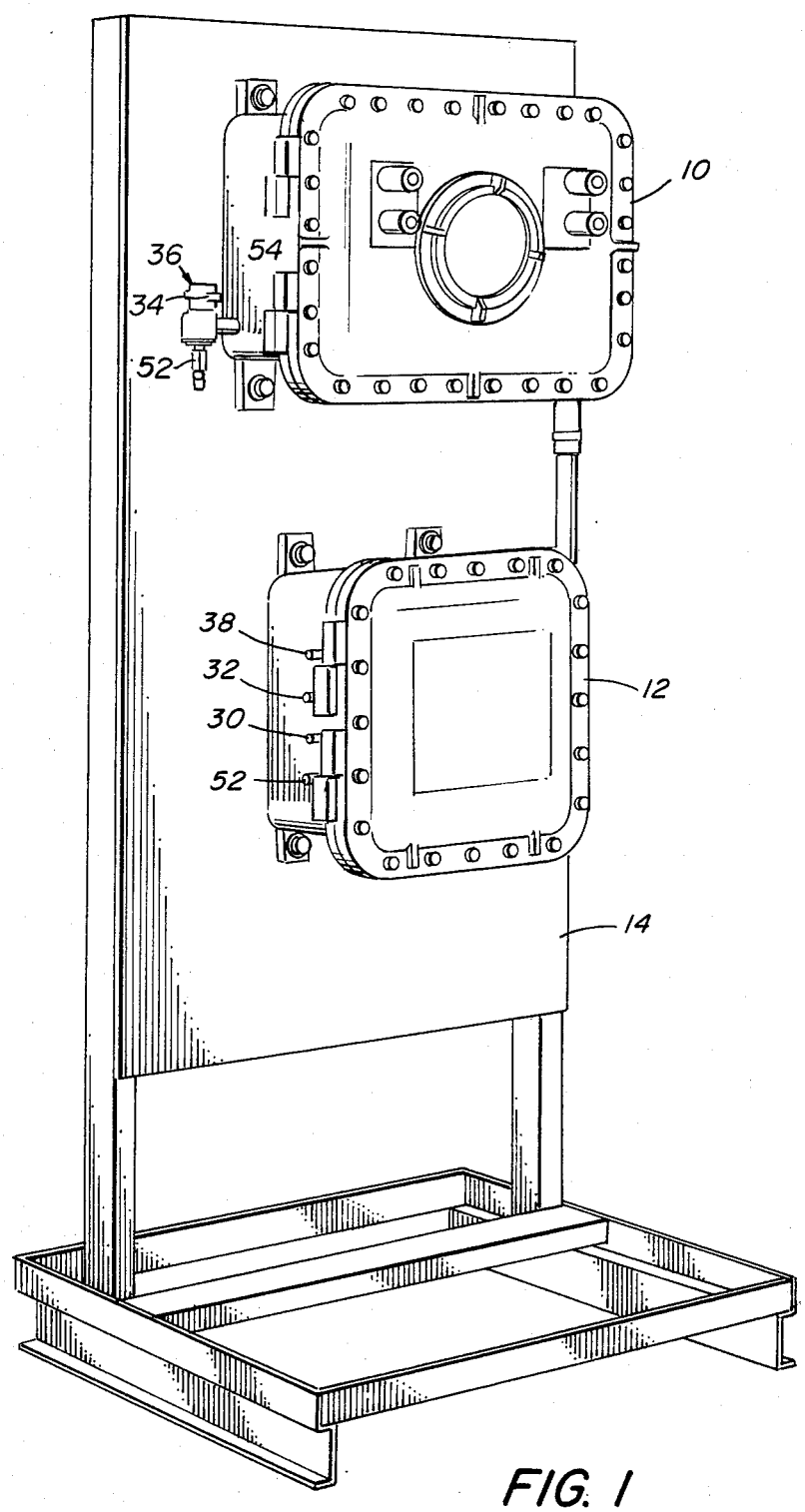
FIG. 1 is a perspective view illustrating the exterior components of an embodiment of the onstream cloud point analyzer constructed according to the invention.
Figure 2:
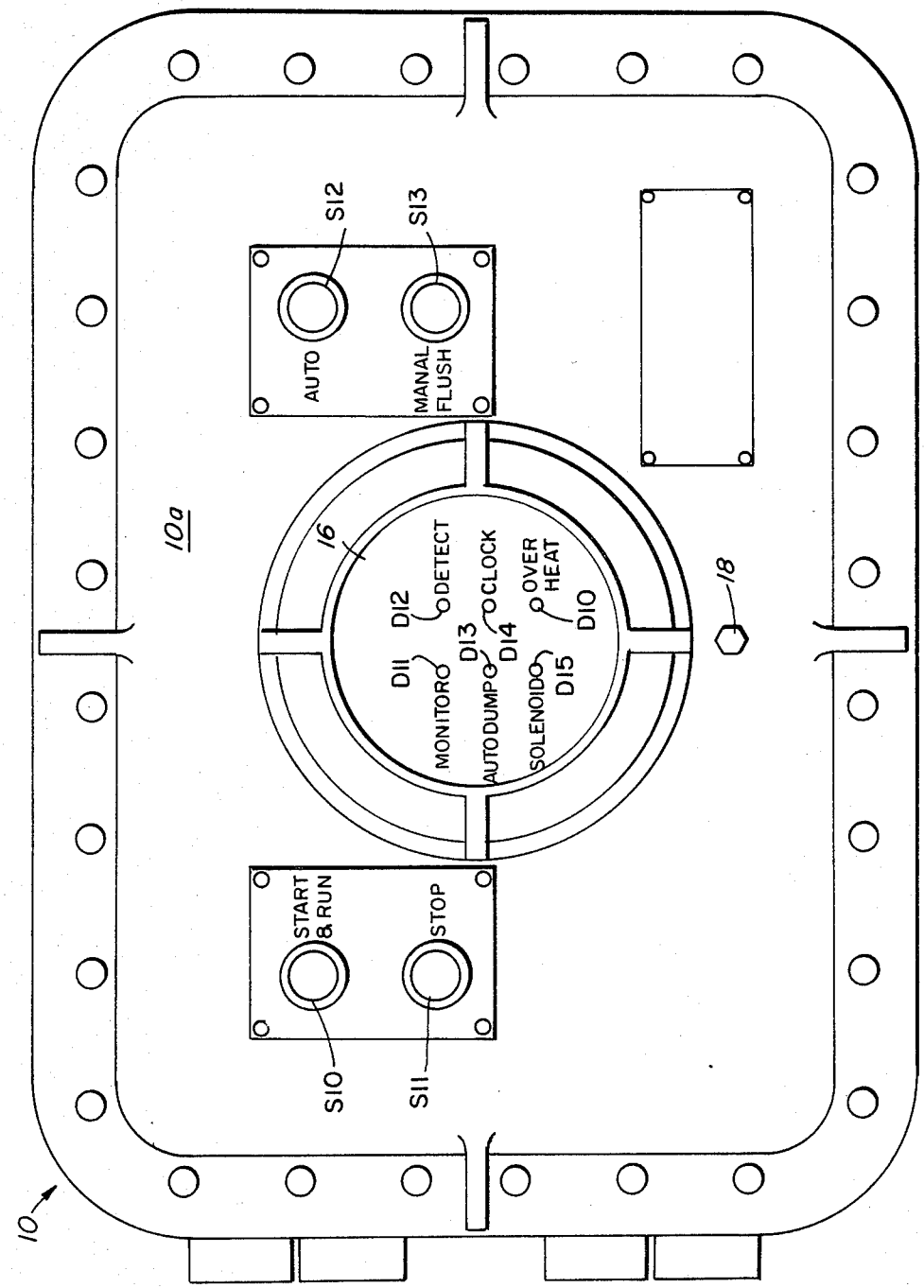
FIG. 2 is a front view of the face of the control box for the analyzer of FIG. 1.

The automatic onstream cloud point analyzer shown in FIG. 1 includes a control box 10 and analyzer box 12 mounted on a rugged free-standing frame 14 designed to be located on the refinery premises near the process line to be sampled. The system is designed to monitor sample stream cloud point temperatures in correlation with ANSI/ASTM (American National Standards Institute/American Society for Testing and Materials) D-2500 and IP (Institute of Petroleum)-219 tests. The instrument's flexible mode automatic operation allows it to handle frequent changes in feedstock characteristics. Thus, the operator can select highspeed trend monitoring (mode 1), simulate laboratory testing (mode 2) or combine the two measurement modes (mode 3). Boxes 10 and 12 form explosion proof housings which can be pressurized if desired to meet Class 1 Group D Division 1 standards for hazardous area applications. The microprocessor controlled system shown in FIG. 1 is designed for use on products as varied as diesel fuel, cycle oil and gas-oil streams with cloud point temperatures as low as −30° C. (−22° F.) with 20° cooling water. The sample measuring apparatus is housed in the lower box 12 separately from box 10 which houses the electronics of the control system as well as the front display panel mounted on the hinged bolted door or cover 10A shown in FIG. 2. The display/control panel includes start and stop pushbuttons S10 and S11 on one side and on the other side pushbuttons S12 and S13 for automatic and manual flush. Buttons S10 through S13 are equipped with self-contained indicator lights. In the central portion of the cover 10A, an array of light emitting diodes (LED's) D10 through D15 are visible through a glass window 16. Below the window 16 is an explosion-proof vent 18 for a pressure transducer for atmospheric sensing.

Figure 3:
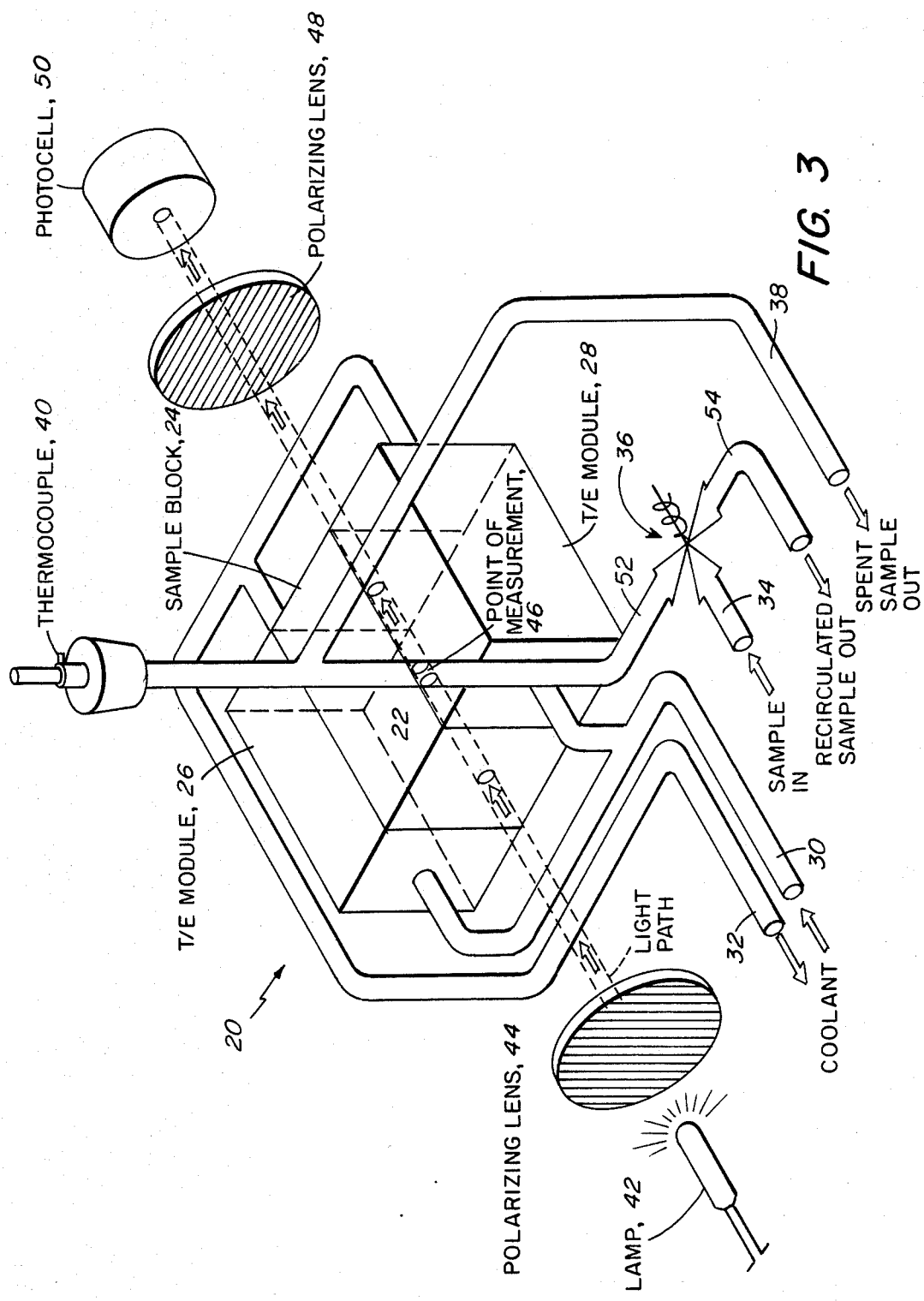
FIG. 3 is a schematic flow diagram of the cloud point analyzer apparatus contained in the lower analyzer box of the unit of FIG. 1.
Figure 4A:
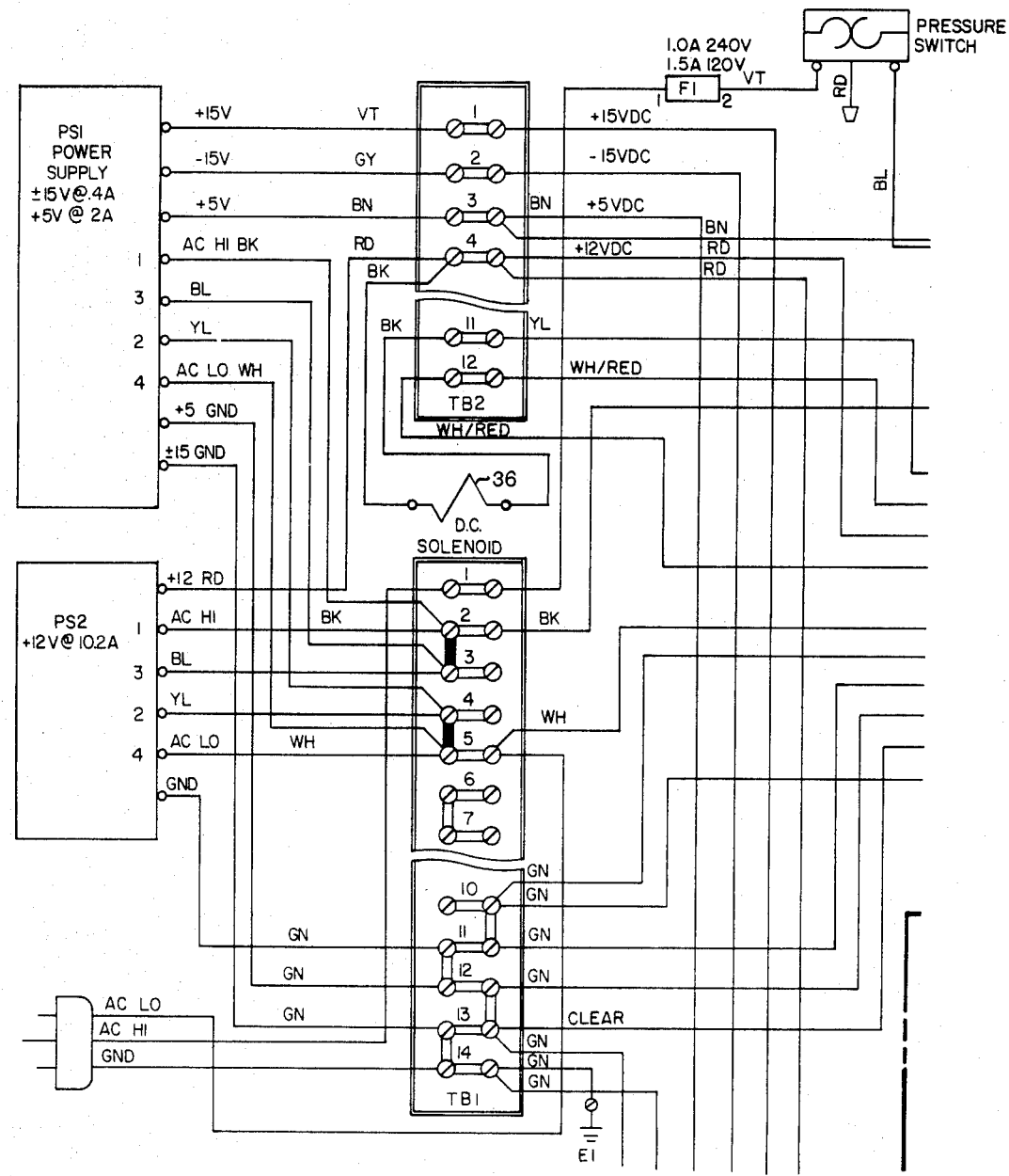
FIG. 4, comprised of FIGS. 4A–4F, is a wiring diagram of the electrical portion of the cloud point analyzer of FIG. 1.
Figure 4B:
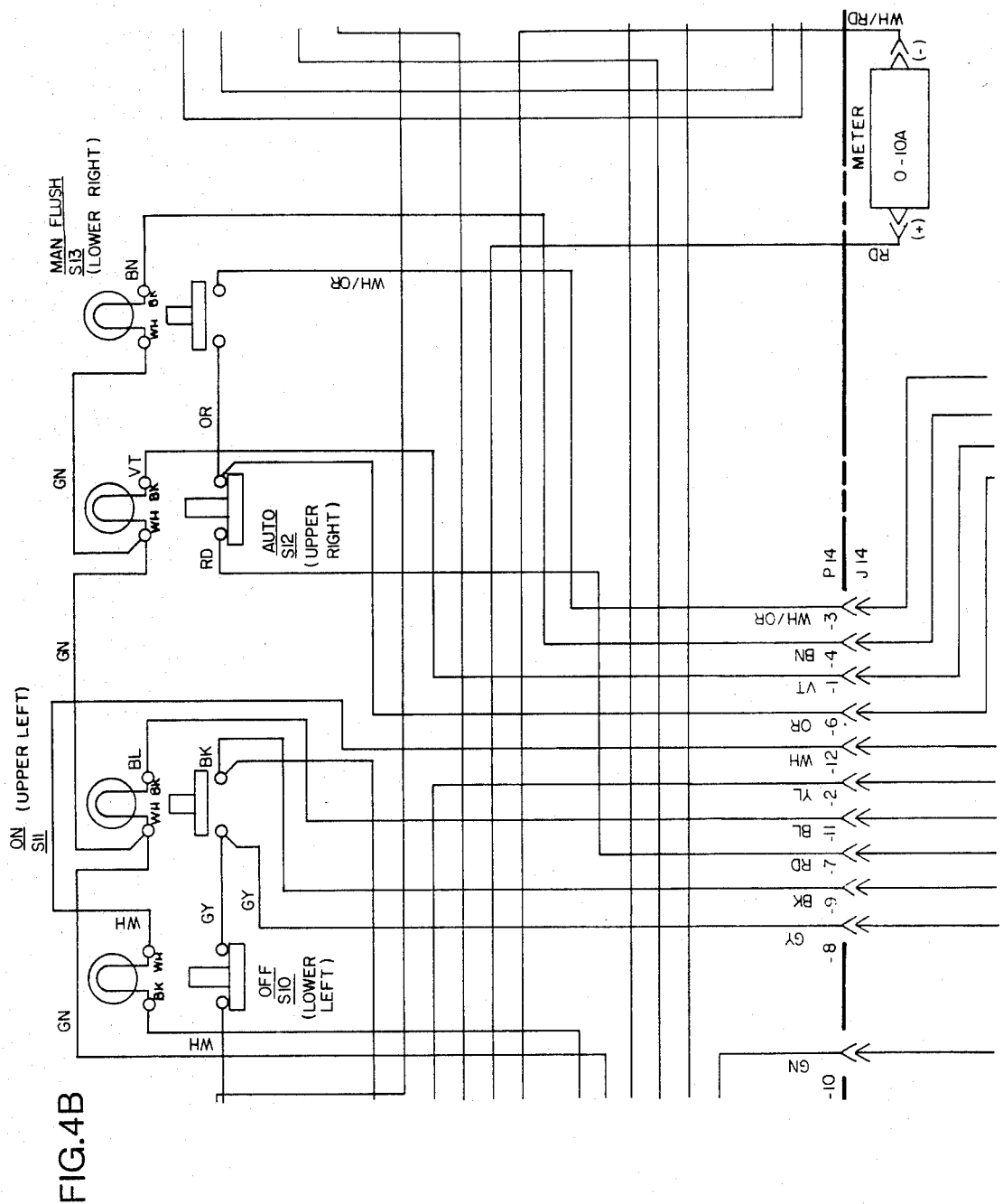
Figure 4C:
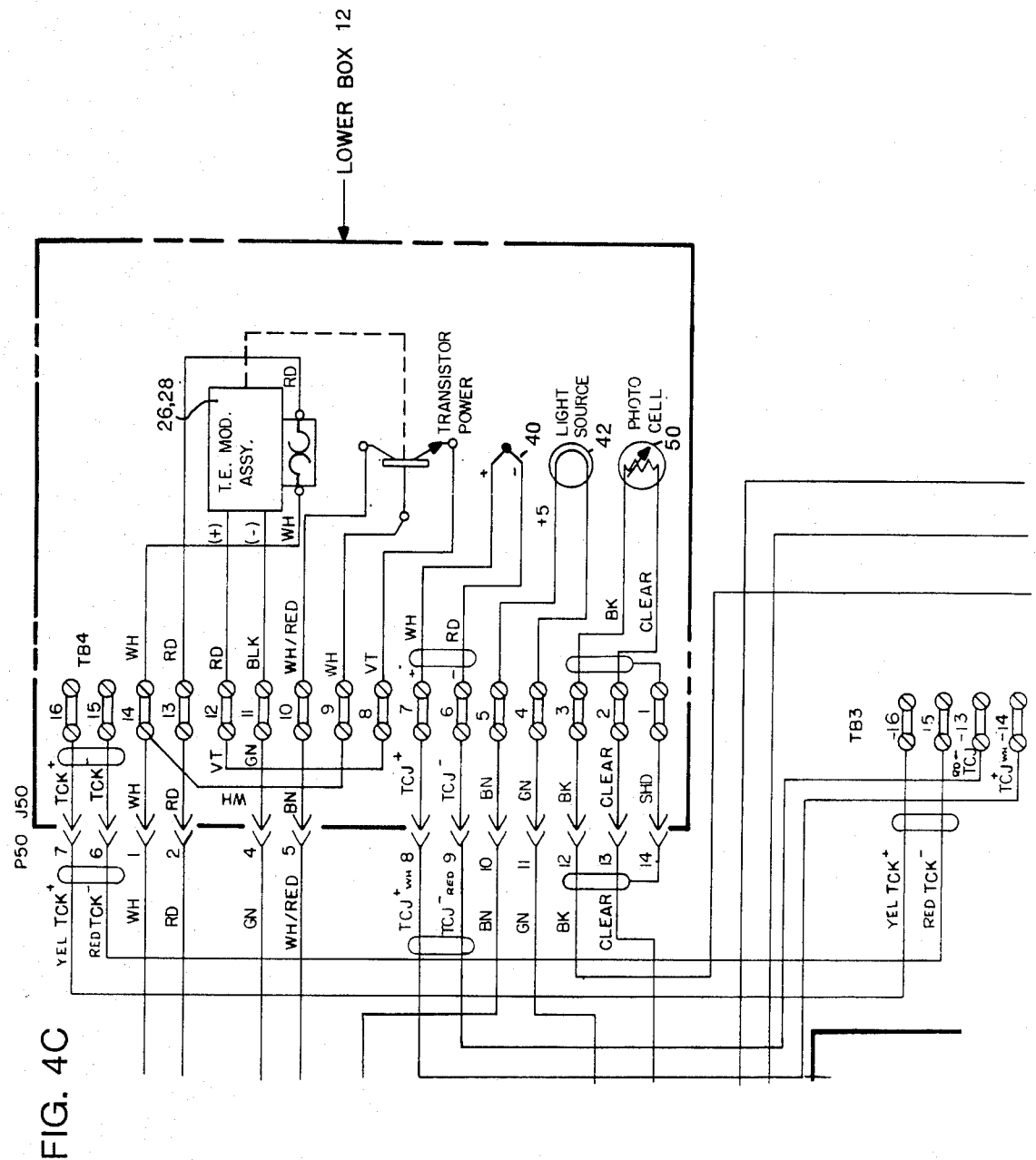
Figure 4D:
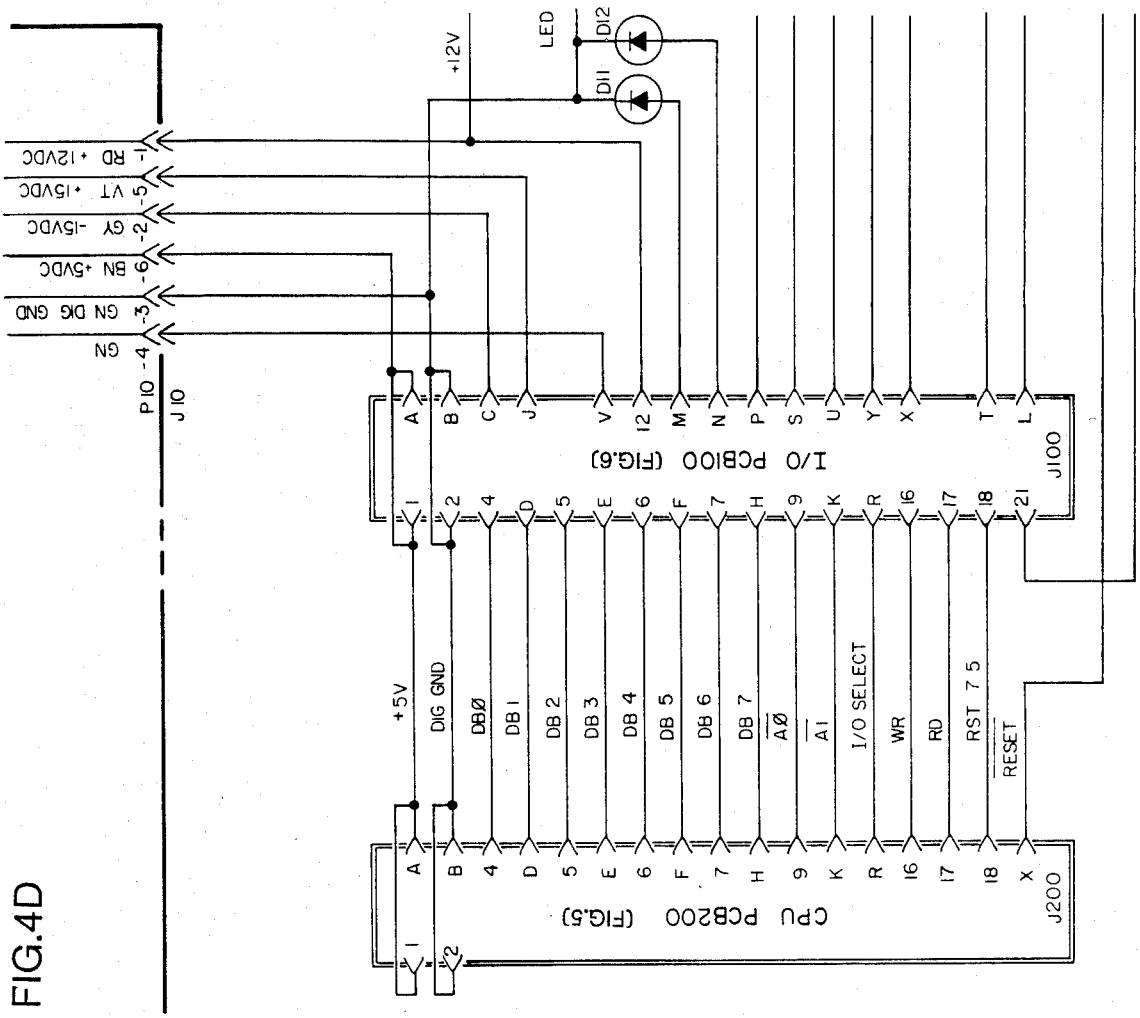
Figure 4E:
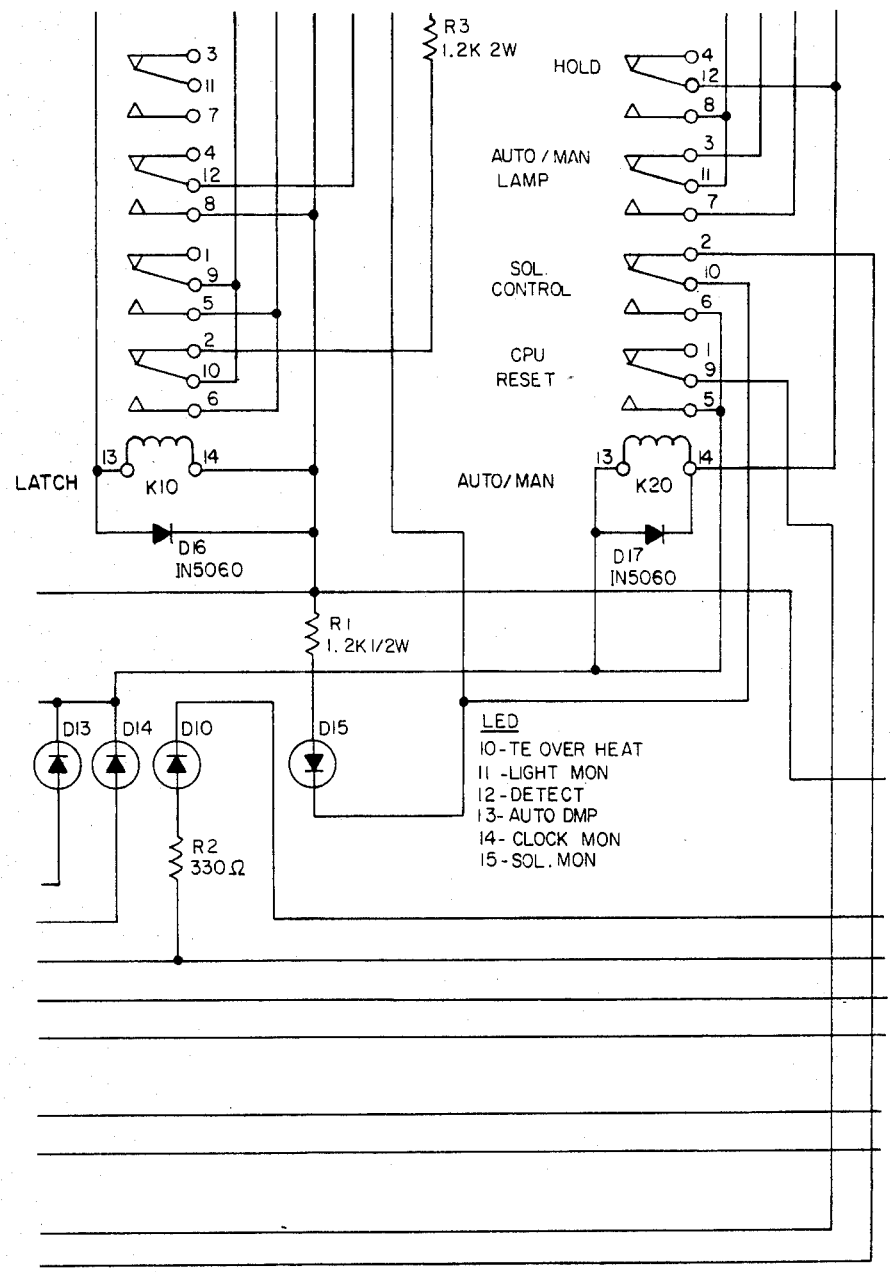
Figure 4F:
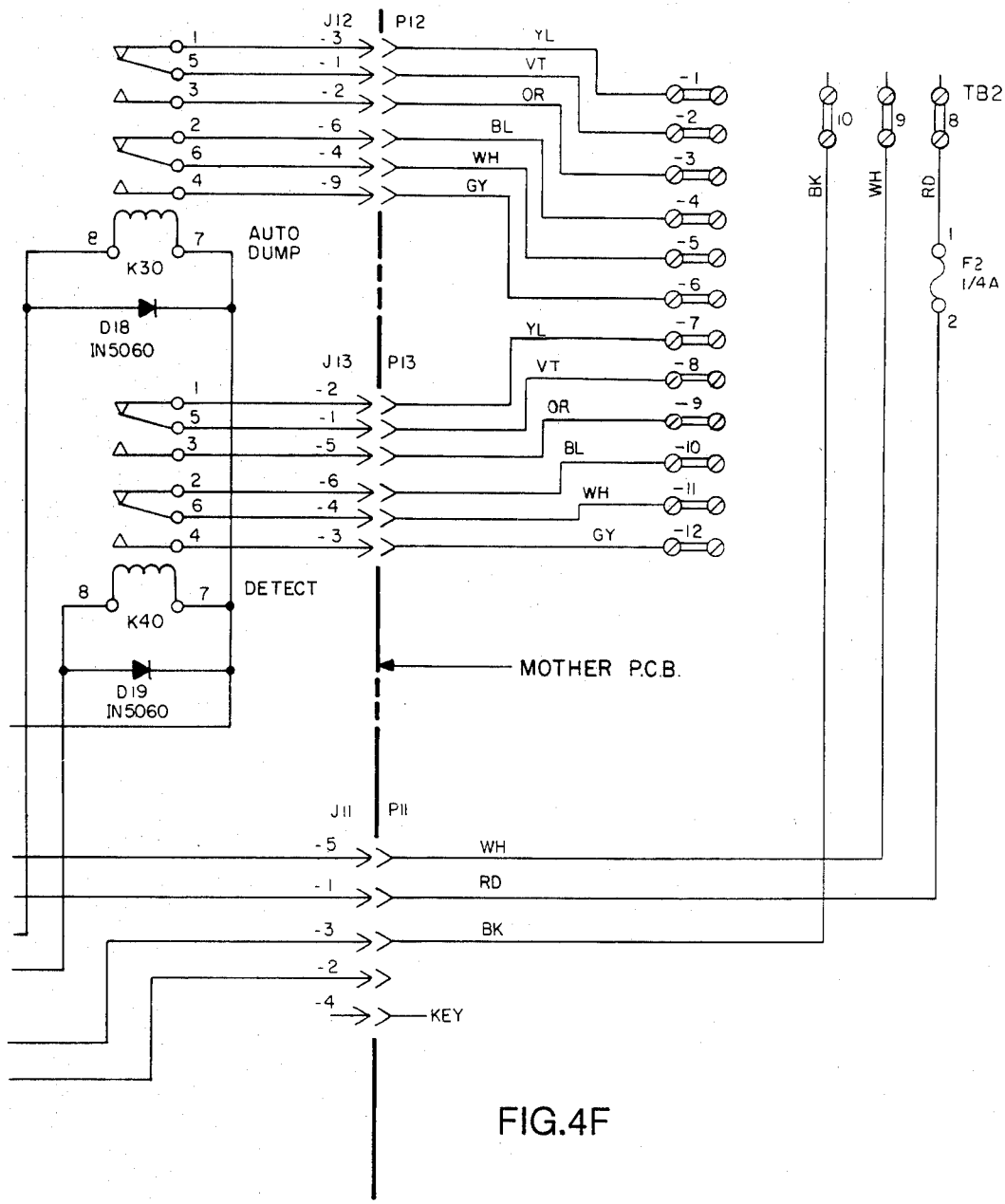
Figures 1, 5A:
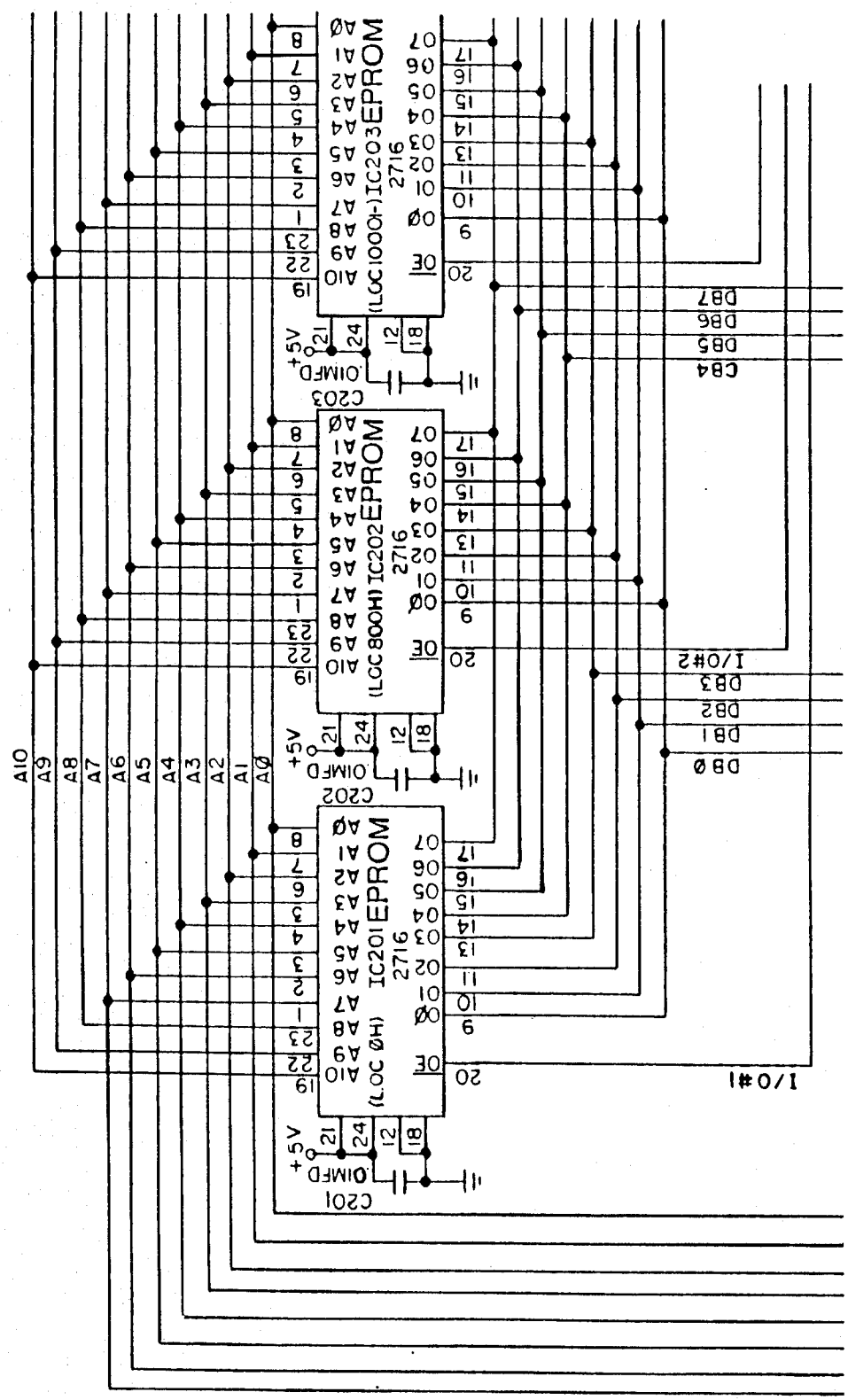
Figures 2, 5A:
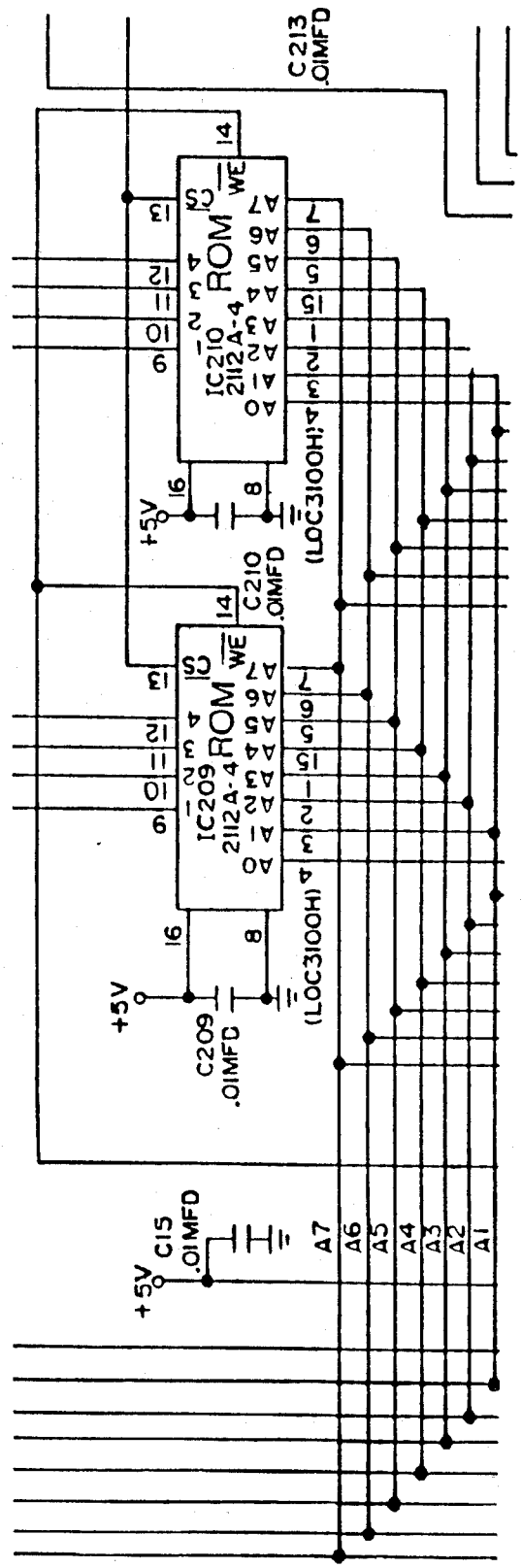
Figures 1, 5B:
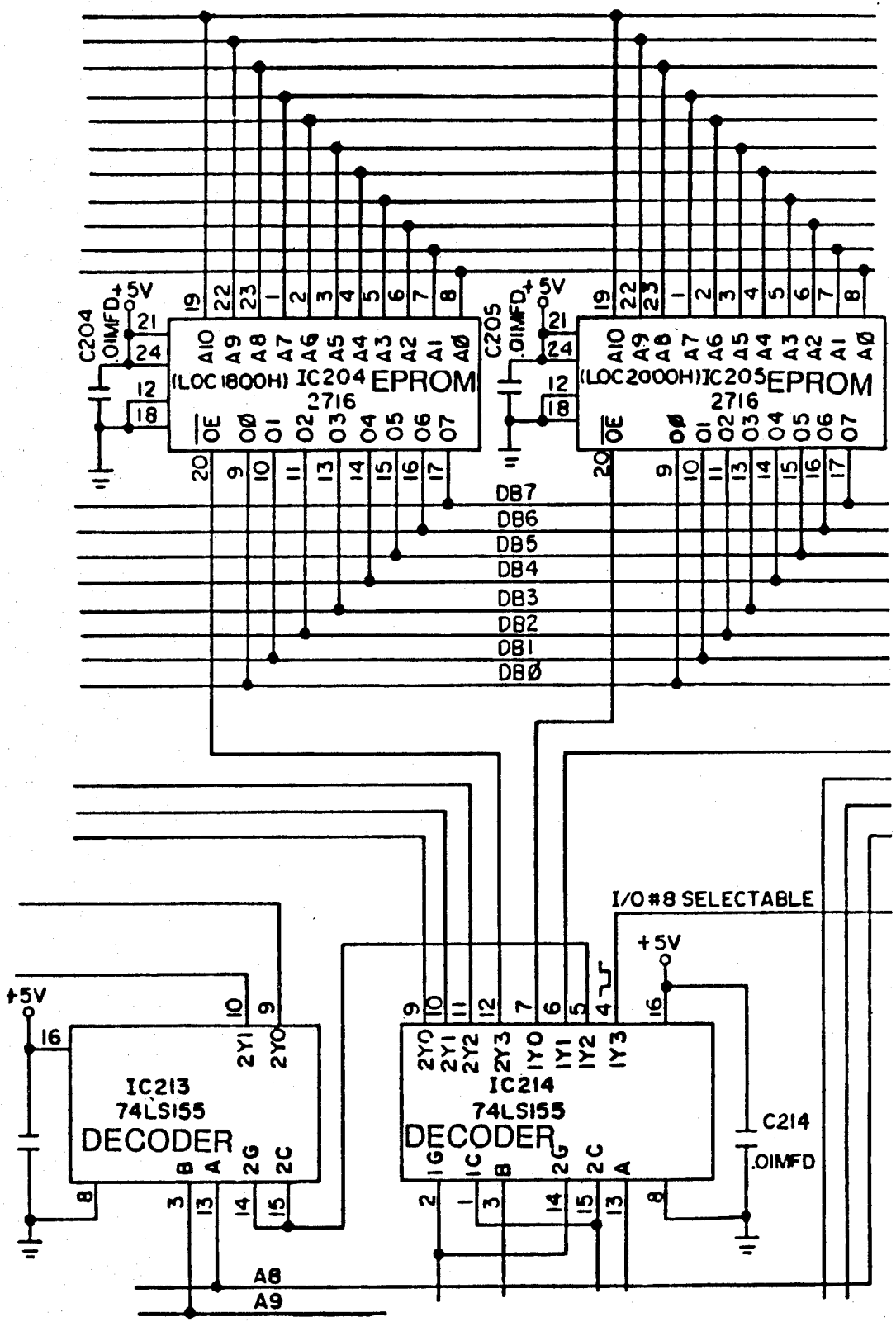
Figures 2, 5B:
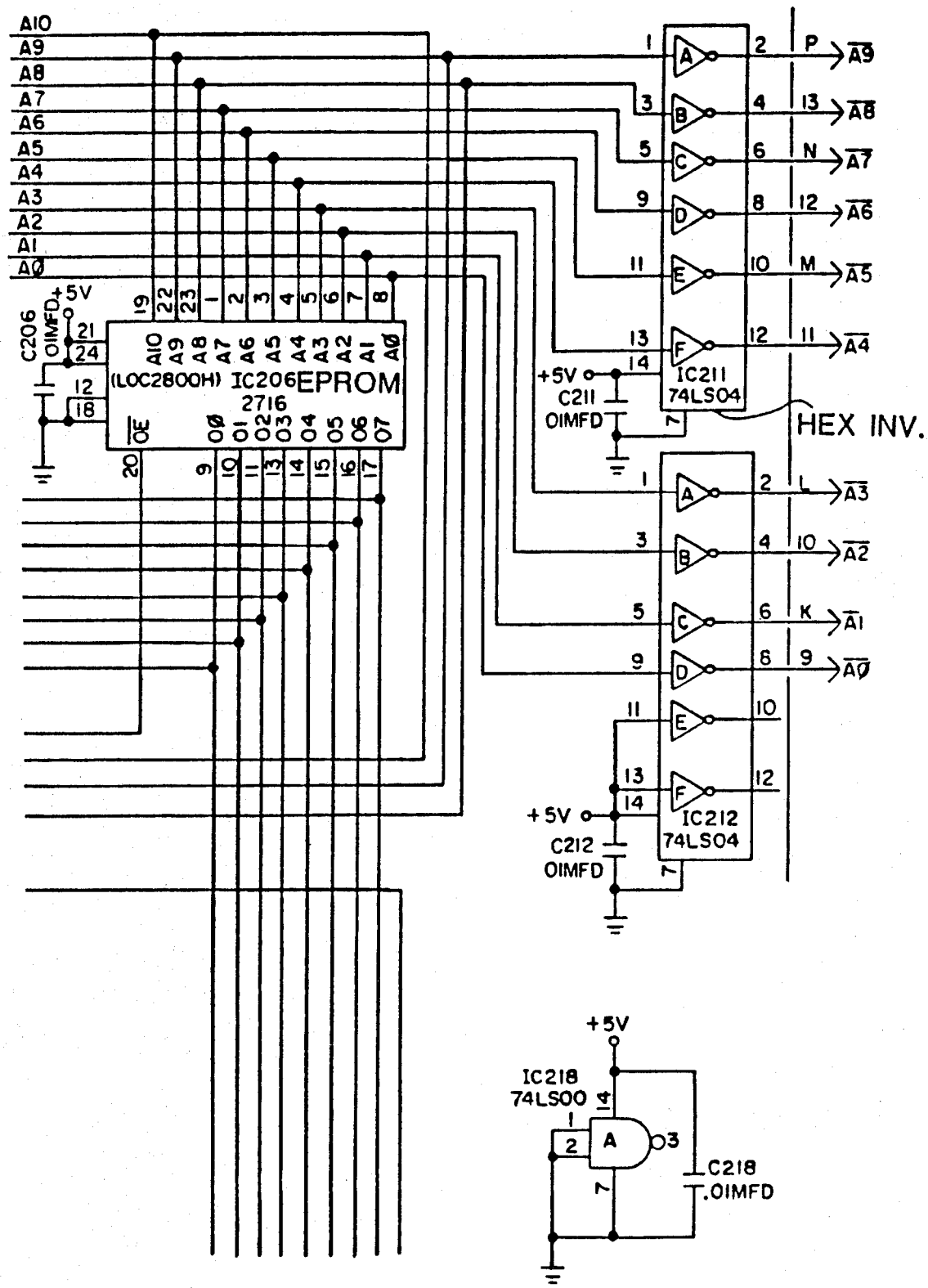
Figures 1, 5C:
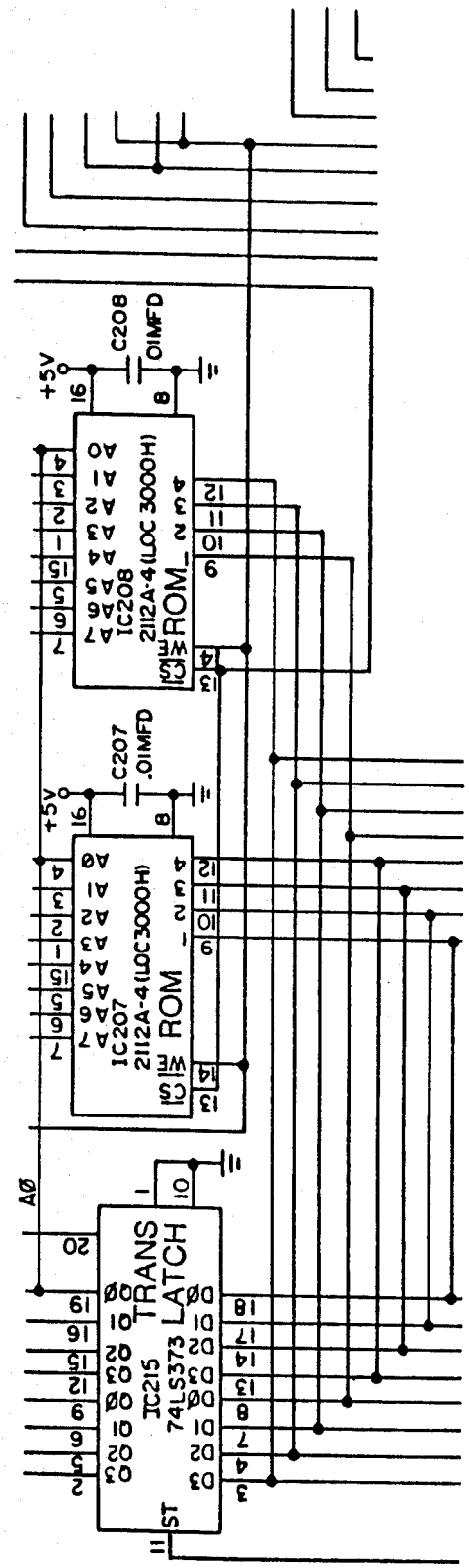
Figures 2, 5C:
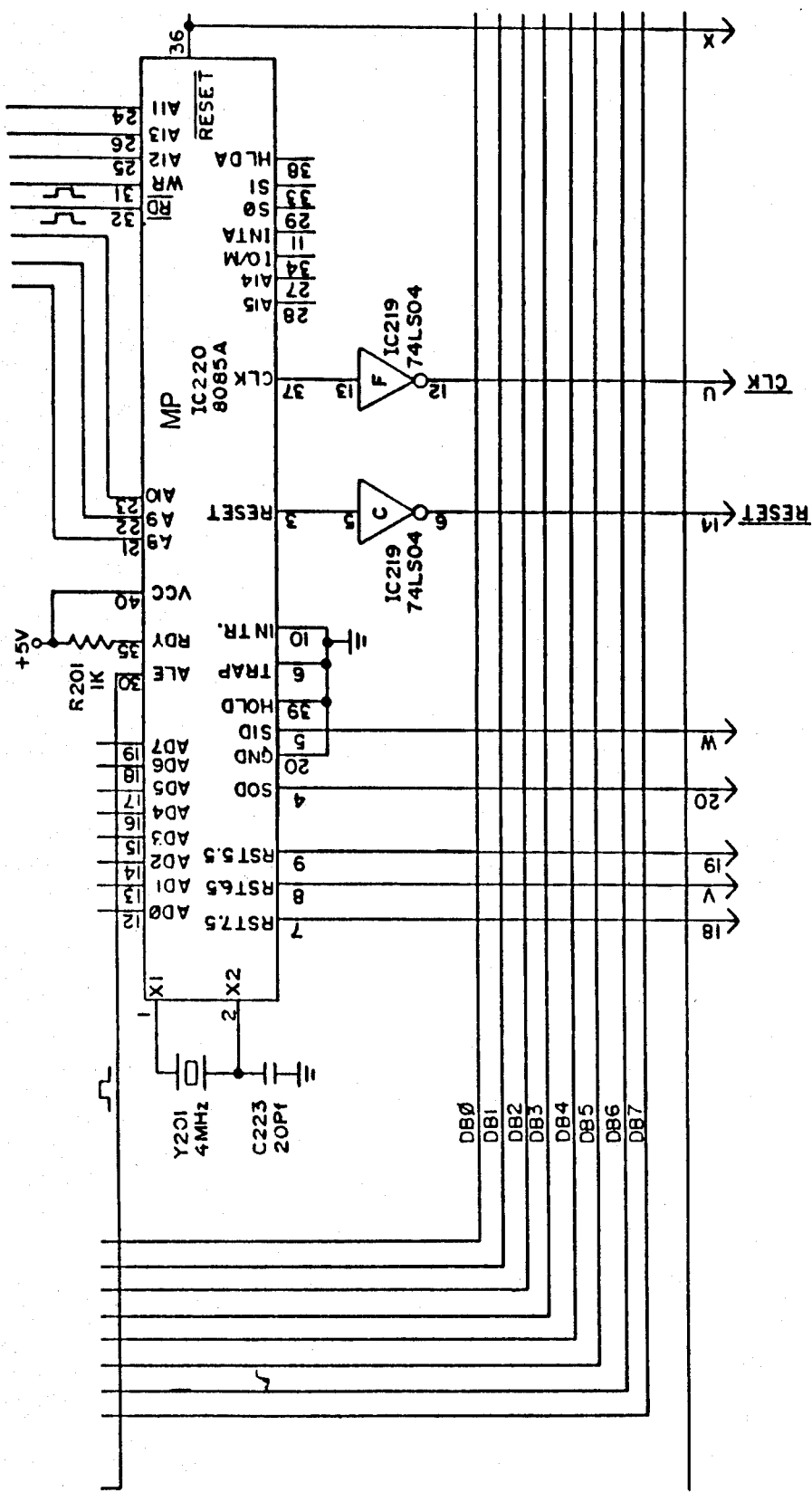
Figures 1, 5D:
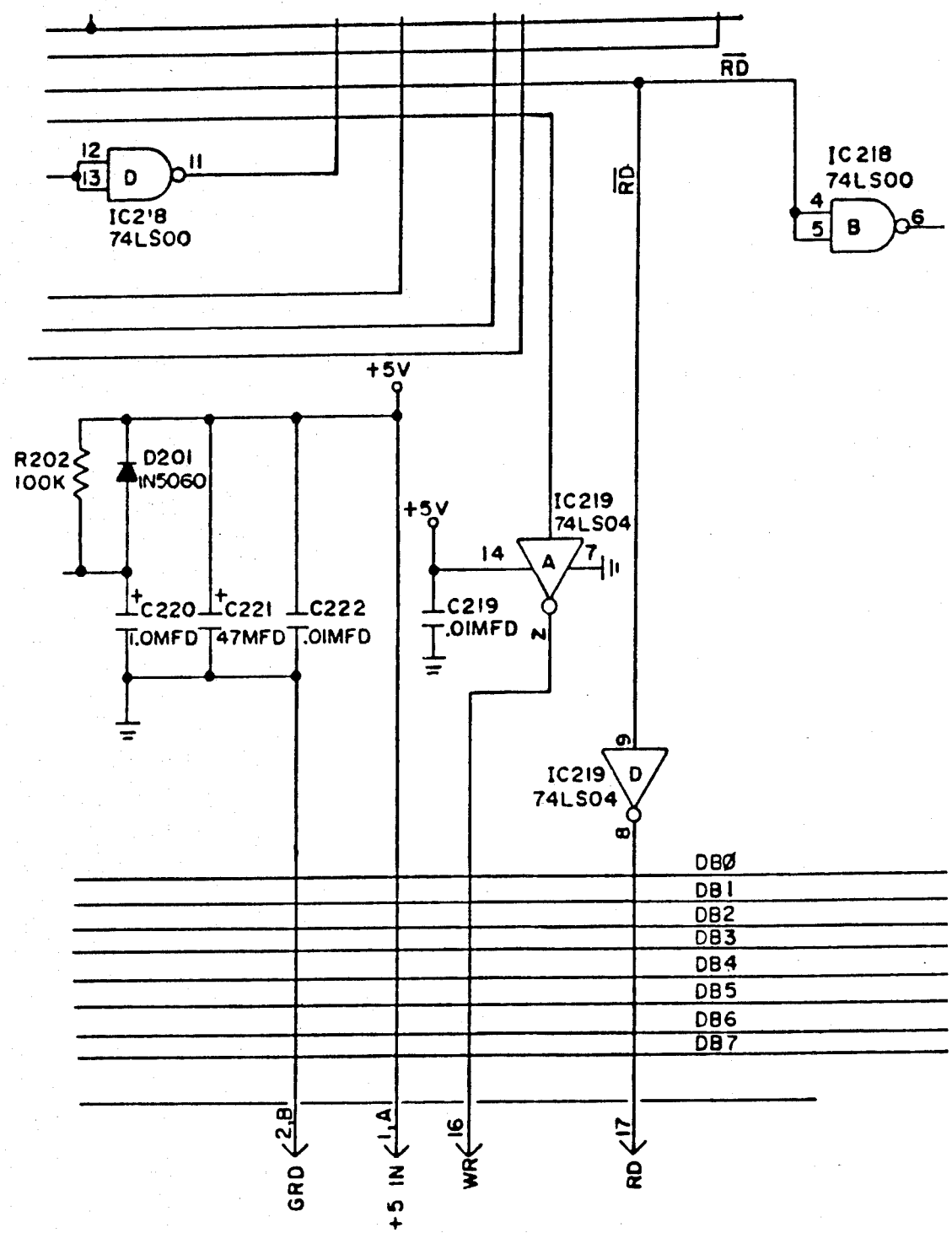
Figures 2, 5D:
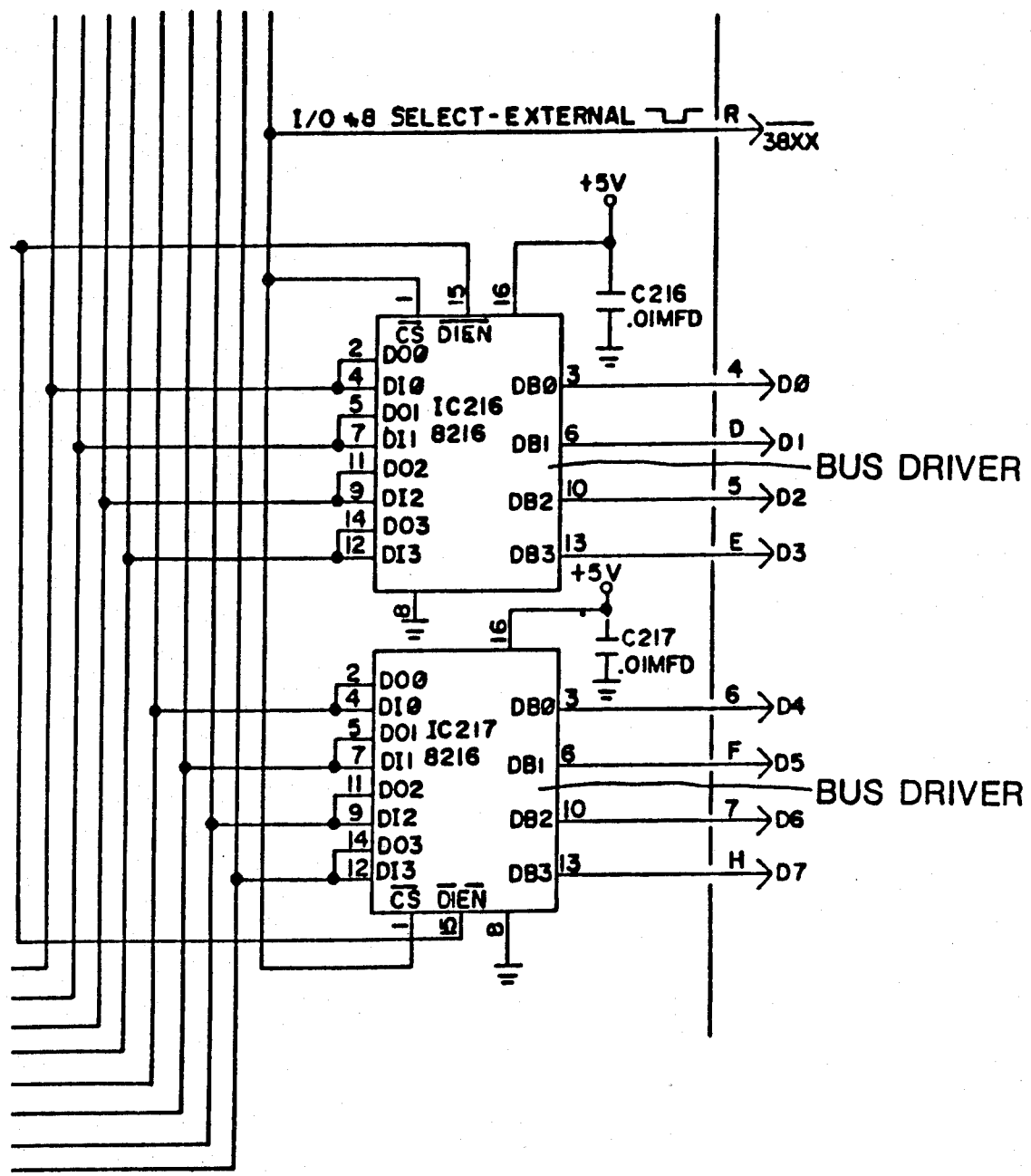
Figure 6A:
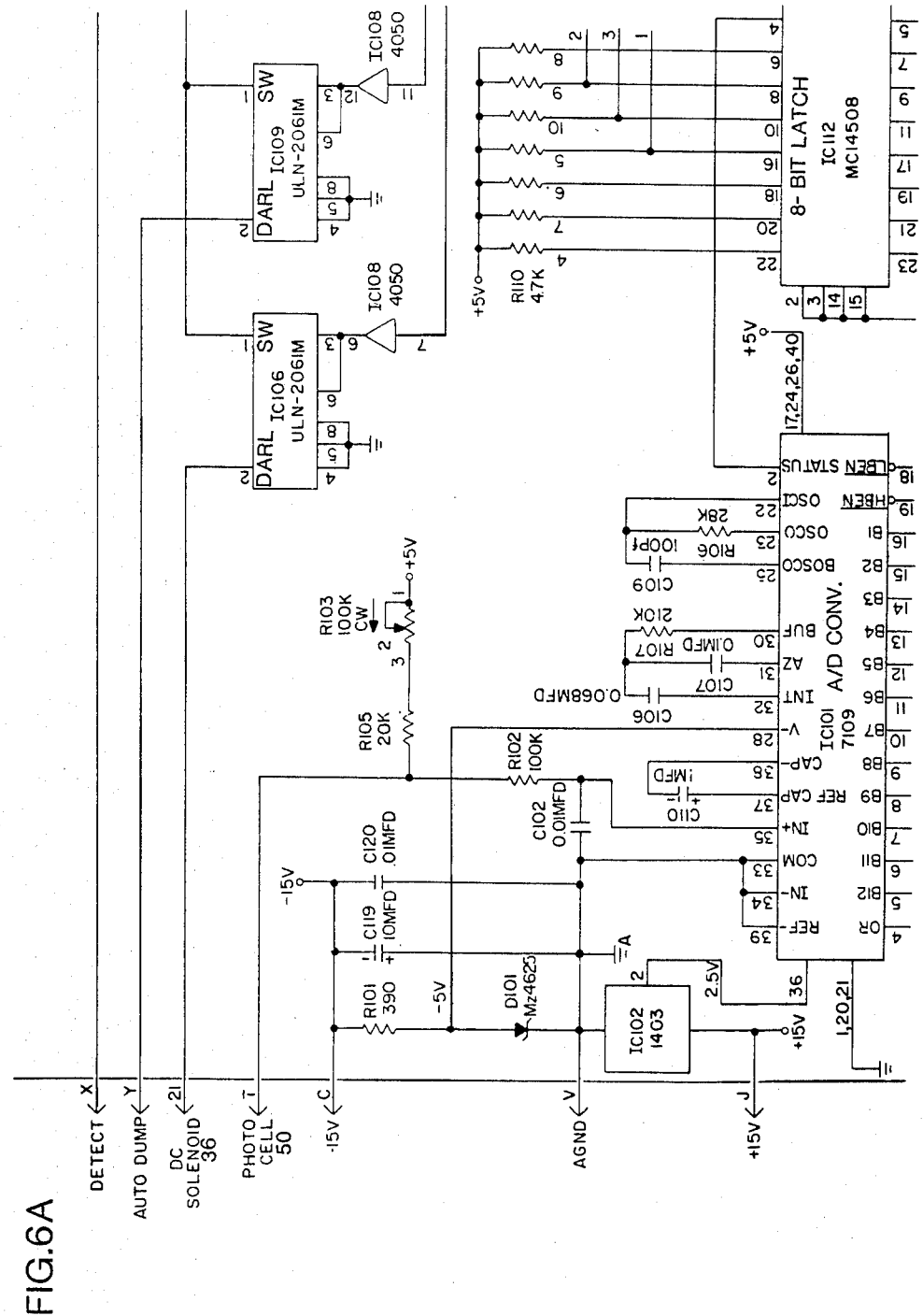
FIG. 6, comprised of FIGS. 6A–6D, is a schematic diagram of the input/output (I/O) PCB of FIG. 4.
Figure 6B:
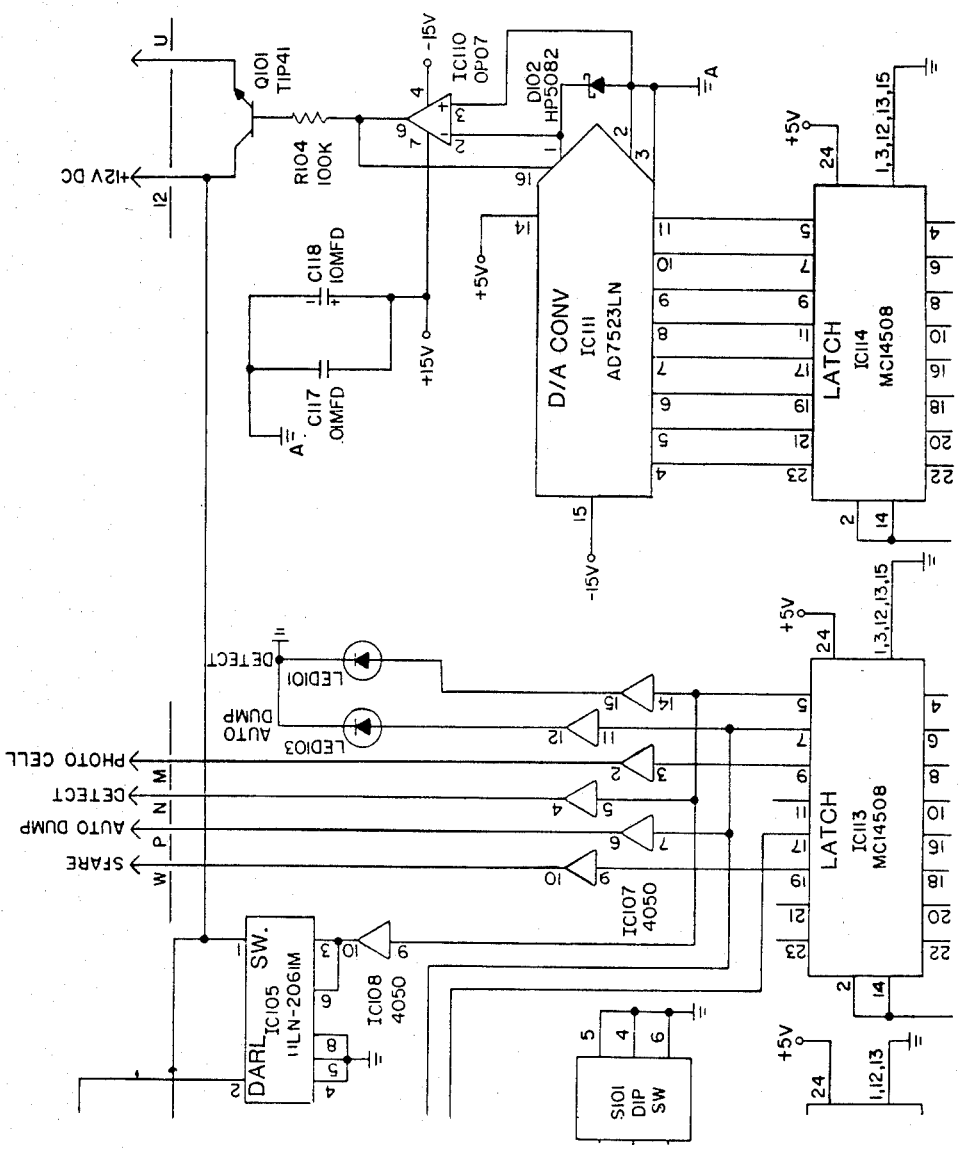
Figure 6C:
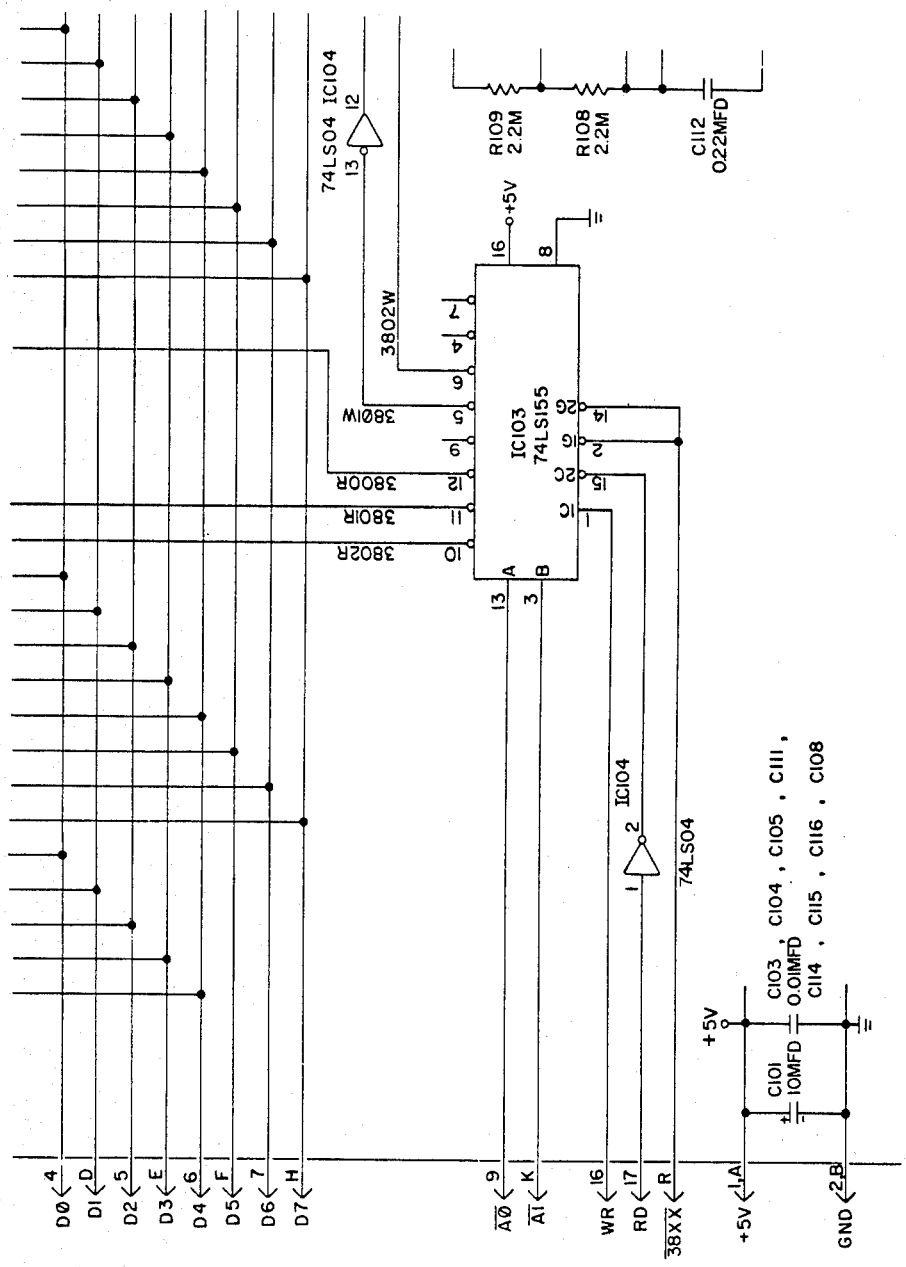
Figure 6D:
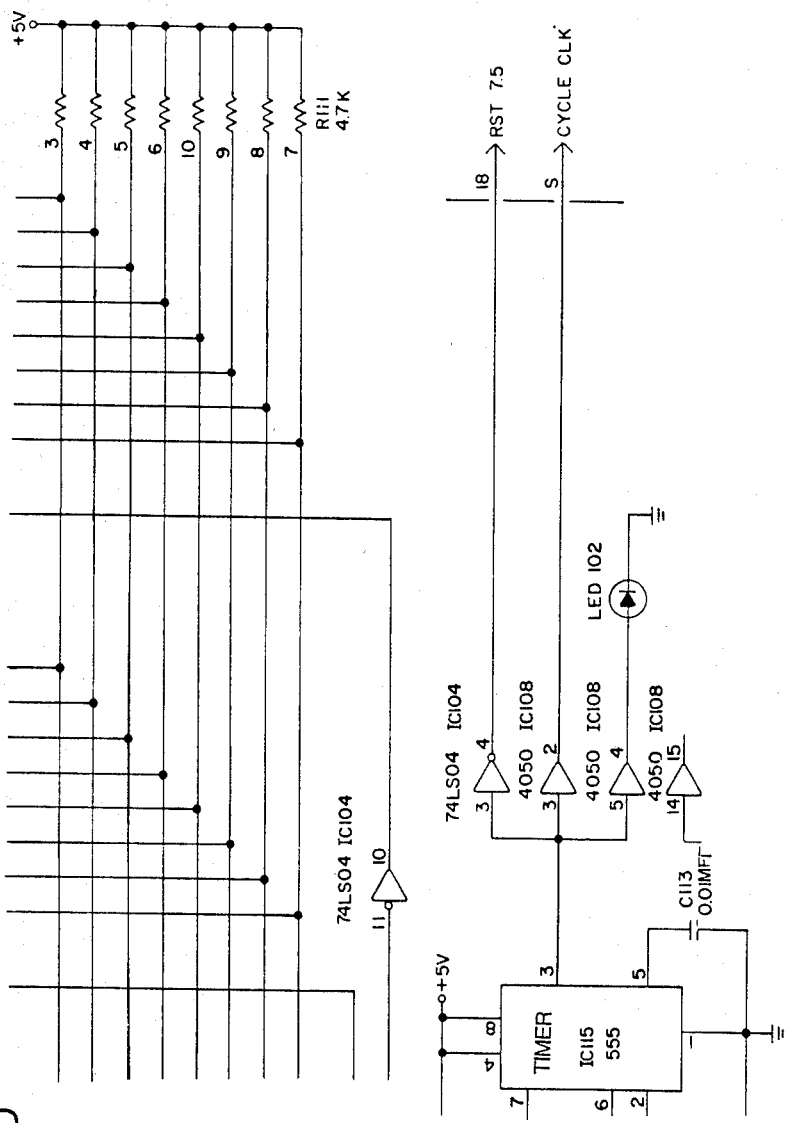

The liquid hydrocarbon sample is cooled in a test cell 20, as shown in FIG. 3, which is thermally isolated and insulated inside the analyzer box 12 (FIG. 1). Test cell 20 includes a vertical glass tube 22 in an aluminum block 24, to which two PELTIER-effect thermoelectric (T/E) cooling modules 26 and 28 are clamped. Liquid coolant is recirculated from coolant inlet line 30 via T/E modules 26 and 28 and out through the outlet line 32. The sample is fed through the test cell 20 from a sample inlet line 34 via a three-way solenoid 36 physically connected to the control box 10 in FIG. 1 and up through the bottom of the vertical glass tube 22 through the test cell and out through a spent sample outlet line 38. Cloud point analyzer sampling valve 36 is a three-way solenoid valve normally deenergized in the bypass mode for recirculating sample. A thermocouple 40 is operatively positioned with respect to the glass tube 22 to monitor the precise temperature of the sample as it passes through the center of the test module. Light rays emanating from an incandescent lamp 42 pass through a first polarizing film 44 which limits their vibration to one plane. The rays then pass through a hole through the test cell 20 intersecting the glass tube 22 at a point of measurement 46 as shown in FIG. 3. The rays pass through the walls of the glass tube, through the sample, through a second polarizing film 48 to an aligned photocell 50. The second polarizing film 48 lies perpendicularly with respect to the first film 44, thus limiting passage of non-refracted light rays into the photocell 50. The electrical resistance of the photocell varies with the amount of light to which it is exposed. Adjusting the sensitivity level of the resistance detection circuits, as explained below, permits the photocell to ignore lesser amounts of light, thus reacting selectively to that refraction attributable to the presence of wax crystal growth in the sample trapped in the tube 22. The sample does not flow continuously through the test cell 20. Rather, a new sample is introduced via the solenoid 36 which thereupon closes to stop further sample liquid from flowing into the test cell during the test. Meanwhile, when the line 52 extending from the solenoid 36 to the test cell is static, the sample withdrawn from the process line is recirculated via line 54 back to the mainstream (not shown).

The sample should be withdrawn from process lines at a point and in a manner conforming to ASTM (American Society for Testing and Materials) procedure D-270. A fast loop sample pump may be installed in the sample inlet line 34 to generate the recommended flow velocity (ideally two to five feet per second) or to establish pressure conditions as demanded by the system. It is also recommended that between the solenoid 36 and the sample pump, a sampling condition system be included with means to filter, coalesce and regulate the sample entering the analyzer. A back check valve and throttling valve are recommended to prevent recirculation of spent sample. Some provision may be made to introduce standardization samples into the analyzer for calibration purposes with suitable pipe fittings and valves. In general use, filtered dry instrument air or nitrogen should be introduced into the analyzer box 12 to prevent condensate accumulation on the super cooled components in the vicinity of the test cell 20.

The heart of the electronic portion (FIGS. 4–7 and Microfiche Appendix I) of the control system for the cloud point analyzer is an Intel 8085 8 bit multiplexed bus microprocessor IC220 shown in the central processing unit (CPU) schematic drawing of FIG. 5. The machine code of FIG. 7 is stored in electronically programmable read only memory (EPROM) IC201 through IC206, representing a total capacity of 16K bytes only a portion of which is actually used by the concise program of Microfiche Appendix I. The EPROM's are addressed via 8 bit transfer latch IC215 which forwards the address lines AD0 through AD7 under the control of the address load enable (ALE) output of the CPU IC220. Additional address lines AD8, 9 and 10 are employed to furnish the complement of the 11 bit address for the EPROM's. The individual EPROM's IC201, IC202, etc. are selected by decoder IC214 under the control of outputs A11-13 of the CPU. The CPU board in FIG. 5 also includes ample random access memory IC207-210 selected in cooperation with decoder IC213. The address lines are passed to the I/O printed circuit board (PCB) shown in FIG. 6 via hex inverter IC211 and the data bus is also furnished to the I/O board via bus drivers IC216 and 217. The CPU IC220 is clocked by a crystal Y201 at 4 MHz. The I/O PCB circuit of FIG. 6 includes three 8 bit latches IC112, 113 and 114 selected by decoder IC103. Latch IC112 is read by port 3800 from decoder IC103 and determines which one of three modes, (1) normal, (2) ramp or (3) combination mode, has been selected. The system output signal from the apparatus described above is the output of the thermocouple 40. The thermocouple output terminals TB3-13 and 14 are designed to be converted to a 4 to 20 milliamp DC signal with a conventional signal converter (not shown). As the thermocouple output is cyclic, representing the alternate heating and cooling sequences of the measuring cycle, a sample and hold circuit may be required in certain situations, for example, for closed loop control of process variables. Otherwise, the thermocouple output can be plotted on a standard X/Y recorder. The peaks on the recorded graph will reliably indicate the cloud point temperature. Independent timer IC115 issues an output signal every second which forms interrupt request RST7.5 to the CPU. The output of the timer IC115 also lights LED D14 on the display panel.

Specific external actions are taken in response to output commands from the CPU via the multiplexed bus. For example, individual bits of latch IC113 are set by the computer at the appropriate time to energize the DC solenoid, for example, via solenoid control in the wiring diagram of FIG. 4, the detect solenoid K40 in FIG. 4 or the auto dump solenoid K30 of FIG. 4. These solenoid control signals are passed by individual bits of IC113 via Darlington switches IC105, 106 and 109. Auto dump and detect output commands also energize lines P and N from the I/O PCB to drive the indicators D12 and D13. Another output bit from IC113 lights the photocell indicator D11. Latch IC114 drives digital to analog converter IC111 which produces a prescribed cooling power rate for the T/E modules 26 and 28. The photocell outupt is passed to analog to digital converter IC101 equipped with voltage reference IC102. The digital output of the analog to digital converter IC101 is placed on the data bus by the decoder IC103 as shown in FIG. 6.

Software instructions in assembly listing form are provided in Microfiche Appendix I. The program consists of the following declarations and routines.

TABLE I

| | |
|---|---|
| RAM | RAM Storage Declarations |
| INIT | Cloud Point Initialize Routine |
| RST 75 | Interrupt RST 7.5 Service Routine |
| FLUSH | Flush Routine |
| DETEK | Detect Routine |
| NORCLD | Normal Cloud Routine (mode 1) |
| RMPCLD | Ramp Routine (mode 2) |
| COMCLD | Combination Routine (mode 3) |
| RTEST | RAM Test Routine |
| CKSUM | Check Sum Routine |

Microfiche Appendix I is a copy of a printout created by an ISIS-II 8080-8085 macroassembler. The memory location in the left-hand column begins at zero for each routine. The order of routines prescribed by the assembler determines the beginning ROM address for each routine in Table I. The term "PUBLIC SYMBOLS" refers to locator symbols for routines or subroutines which are used elsewhere in the program. The term "EXTERNAL SYMBOLS" refers to routines or subroutines external to the subject routine, for example, the interrupt routine is "jumped to" at relative ROM location 3C in the cloud point initialize routine. The assembly language and address of the operand are given in the columns labelled Source and Statement, respectively, to the right of which are annotations which describe the function.

The cloud point initialize routine initializes the cloud point hardware and software to known states and runs a self-diagnostic test of EPROM's and RAM's.

Each measuring cycle begins with the introduction of a sample into the test cell via the solenoid valve 36. The test cell is first flushed clean of any previous residue for 30 to 60 seconds, depending on whether mode 1 or mode 2 operation has been selected. Then the solenoid valve is deenergized, trapping fresh sample in the measuring cell and initiating a cooling sequence. In mode 1 operation, the microprocessor initially controls power to the cooling modules 26 and 28 via the D to A converter IC111 of FIG. 6 to achieve the maximum cooling rate. This quickly establishes the preliminary cloud point temperature. The photocell 50 signals the first appearance of wax crystals by a significant change in its electrical resistance. The analog to digital converter IC101 of FIG. 6 is read via an output command. Upon detection of this change in electrical resistance, the old sample is flushed via the solenoid 36 and a new sample is trapped. After each measurement cycle, the microprocessor readjusts the cooling power so that the time interval between termination of the flush cycle and detection of cloud point is brought back toward a nominal value of 90 seconds. This feature allows the analyzer to react to changes in feedstock. The reference level or baseline to which the photodetector output level is compared is automatically stored and updated to reflect changes in feedstock properties.

Should full power be applied without detection of a cloud point, the microprocessor automatically initiates an auto dump sequence, flushing the cell before repeating the test. An auto dump counter in software counts the number of auto dumps. Should three cycles occur without detection, a nine minute flush cycle will commence in order to remove any deposits that have accumulated on the inner walls of the glass tube.

In mode 2, the microprocessor gradually increases the cooling rate to simulate laboratory test conditions. If a cloud point is not detected, full power and minimum temperature, and 20 minutes elapses, the analyzer dumps the sample, flushes for three minutes and repeats the cycle.

Mode 3, a combination of modes 1 and 2, consists of 120 cycles of mode 1 operation followed by a single mode 2 cycle. The power required to reach cloud point in mode 2 is sensed by the microprocessor and this setting is used for the testing in mode 1.

Using the above described system, refineries can realize dramatic savings. Capacity for self-adjustment to sample characteristics and self-diagnosis has been incorporated into the analyzer's fully automatic operation. The system's unique design provides automatic shutdown in the event of coolant system malfunction or loss of case pressurization. LED displays keep the operator informed of the analyzer status, including flush, detection, auto dump, internal timing cycles and detection of sample cell component failure.

The foregoing description is of a preferred embodiment and is given by way of illustration. Many variations, adaptations, additions or omissions of specific components can be made by those skilled in the art without departing from the spirit or scope of the invention as indicated by the appended claims and the equivalents thereto.

What is claimed is:

1. Cloud point analyzer apparatus of the type having a cooling module for cooling a sample at variable cooling rates in accordance with a variable cooling power input, a sample cell for liquid hydrocarbons mounted in said cooling module, sensor means for producing an electrical sensor output indicative of the optical properties of the sample characteristic of cloud point, thermocouple means for producing an electrical output indicative of the temperature of said sample in said cell, and means for recording a value corresponding to said thermocouple means output, wherein the improvement comprises means responsive to an change in the level of said sensor output for issuing a cloud point detection signal, means responsive to said detection signal for automatically discharging a given liquid hydrocarbon sample and recharging the sample cell with a new sample, and control means for automatically adjusting the cooling power input to a new fixed level after each sample if a time interval between initial charging of the previous sample and cloud point detection is outside a predetermined range so as to bring said time interval within said range, whereby said time interval is controlled by said control means adjusting a discrete power input level from sample to sample.

2. The apparatus of claim 1, wherein the time interval is nominally ninety seconds.

3. The apparatus of claim 1, wherein said control means includes means for initially setting said cooling power input to a maximum level,
    whereby an initial cloud point is quickly obtained, after which the power is automatically adjusted downwards as necessary to come within the desired time interval range.

4. The apparatus of claim 1, wherein said control means includes
    means for applying a gradually increasing cooling power input to said cooling module until an initial cloud point is achieved,
    means for maintaining said initial cloud point power input level as a fixed power level for the next sample,
    whereby the first discrete cooling power setting is variable up to a maximum level, after which it is automatically adjusted upwards or downwards as necessary to come within the desired time interval range.

5. Cloud point analyzer apparatus of the type having a cooling module for cooling a sample at variable cooling rates in accordance with a variable cooling input power, a sample cell for liquid hydrocarbons mounted in said cooling module, sensor means for producing an electrical sensor output indicative of the optical properties of the sample in the cell characteristic of cloud point, thermocouple means for producing an electrical output indicative of the temperature of said sample in said cell, and means for recording a value corresponding to said thermocouple means output, wherein the improvement comprises
    means responsive to an change in said sensor output level for issuing a cloud point detection signal,
    means responsive to said cloud point signal for automatically discharging a given liquid hydrocarbon sample and recharging the sample cell with a new sample,
    counter means for issuing a first mode change signal following the occurrence of a predetermined number of cloud point detection signals,
    means responsive to said first mode change signal for controlling the cooling power to gradually increase the cooling rate from a first level to a predetermined maximum level,
    auto dump means for discharging said sample and recharging said cell with a new sample if a cloud point signal has not occurred and the cooling power has reached said predetermined maximum level and a predetermined time interval has elapsed,
    means responsive to the occurrence of a cloud point detection signal while said cooling power is being gradually increased for storing a value indicative of the cooling power level at the time of said cloud point detection signal for discharging said sample and recharging said cell with a new sample and for issuing a second mode change signal,
    means responsive to said second mode change signal for disabling said cooling power increasing means and for maintaining the stored cooling power level while proceeding to detect cloud point of the new sample.

6. The apparatus of claim 5, wherein the improvement further comprises the means for controlling the cooling power level before the first mode change signal and after the second mode change signal by adjusting the cooling power input to a new fixed level if the time interval between the initial charging of the previous sample and cloud point detection signal is outside a predetermined range so as to bring said interval within said range,
    whereby a prescribed number of controlled interval cycles at discrete power levels is followed by a single variable power cycle which in turn is followed by controlled interval cycles at discrete power levels beginning with the power level attained at cloud point in the variable power cycle.

* * * * *